United States Patent
Mero et al.

(10) Patent No.: US 6,794,551 B2
(45) Date of Patent: Sep. 21, 2004

(54) PROCESS FOR PRODUCING PROPARGYL BROMIDE

(75) Inventors: Christopher L. Mero, State College, PA (US); Hassan Y. Elnager, Baton Rouge, LA (US); Robert C. Herndon, Jr., Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 218 days.

(21) Appl. No.: 10/231,571

(22) Filed: Aug. 30, 2002

(65) Prior Publication Data

US 2004/0044259 A1 Mar. 4, 2004

(51) Int. Cl.$^7$ .......................... C07C 17/00; C07C 17/02; C07C 17/04; C07C 17/08; C07C 21/00; C07C 23/00
(52) U.S. Cl. ........................................ 570/217; 570/216
(58) Field of Search .................................. 570/217, 216

(56) References Cited

U.S. PATENT DOCUMENTS

| 2,794,727 A | 6/1957 | Barrons |
| 5,910,617 A | 6/1999 | Lecomte et al. |
| 6,291,731 B1 | 9/2001 | Stamm et al. |

FOREIGN PATENT DOCUMENTS

| GB | 925147 | 5/1963 |
| SU | 767081 | 9/1980 |

OTHER PUBLICATIONS

Barrons, Keith C.; "Methyl Bromide Alternative: Propargyl Bromide"; Farm Chemicals International; Nov. 2000; pp. 35–36.

Black, D.K. et al.; "Convenient Syntheses of Pure Allenic And Acetylenic Bromides"; Tetrahedron Letters, No. 8; 1963; pp. 483–486.

Forshey, D.R. et al.; "Potential Hazards of Propargyl Halides and Allene"; Bureau of Miines, USA Fire Technology, 1969; vol. 5, Issue 2; pp. 100–111.

Guedin–Vuong, Denis et al.; "An Easy Access to Homopropargylic Ethers"; Bulletin De La Societe Chimique De France; 1986; No. 2; pp. 245–252.

Henry, Louis; "On the Propargyl Compounds (Provisional Report)"; Chem. Ber.; vol. 6; 1873 pp. 728–730 (translation 4 pages); Non–translation (4 pages).

Kirrmann, A.; "Preparation du bromure de propargyle"; Bull Soc. Chim. Fr.; 1926; pp. 698–699.(not translated).

Konovalova, E. P. et al.; "Synthesis And Properties of Certain n–Propargylphenothiazines And Their Cation Radicals"; Chemistry of Heterocyclic Compounds; vol. 29; No. 10; 1993; pp. 1222–1225.

*Primary Examiner*—Elvis O. Price
(74) *Attorney, Agent, or Firm*—Edgar E. Spielman, Jr.

(57) ABSTRACT

This invention provides a process of producing propargyl bromide in the absence of a base. The process comprises:

A) bringing together in a reaction zone under an inert atmosphere and in the absence of a base and in the presence of an inert diluent, a feed of phosphorus tribromide and a separate feed of propargyl alcohol thereby forming a reaction mixture;
B) while mechanically agitating the mixture being formed in A), maintaining the temperature of the mixture in the range of about 0° C. to about 25° C. to form a product mixture, and then
C) raising the temperature of the product mixture to a temperature in the range of about 40° C. to about 60° C. while stirring the product mixture for a ride period of at least about 2.5 hours.

Such process can be conducted as a batch process, as a semi-batch process, or as a continuous process.

20 Claims, No Drawings

PROCESS FOR PRODUCING PROPARGYL BROMIDE

REFERENCE TO RELATED APPLICATIONS

Commonly-owned copending application Ser. No. 10/118,290, filed Apr. 8, 2002, by us and some of our colleagues, describes and claims stabilized propargyl bromide compositions, and processes for preparing propargyl bromide in the presence of an amine, and a method of controlling pests. Commonly-owned copending application Ser. No. 10/126,260, filed Apr. 18, 2002, by us and some of our colleagues, describes and claims stabilized propargyl bromide compositions, processes for preparing propargyl bromide in the presence of an amine, and a method of controlling pests.

BACKGROUND

Propargyl bromide (3-bromopropyne) is known to be useful as a soil fumigant for control of fungi, nematodes, and undesirable plant life. See for example U.S. Pat. No. 2,794,727. It is believed that propargyl bromide is a good replacement for methyl bromide. See K. C. Barrons, *Farm Chemicals International*, 2000 35–36.

A typical process for producing propargyl bromide involves low temperature initiation of reaction of propargyl alcohol and phosphorus tribromide in a liquid phase in the presence of base which usually is a tertiary amine such as triethylamine. While workable, undesirable amounts of waxy solids are often formed in the reaction mixture. Further, because the reaction is exothermic, the requirement for low temperatures (e.g., 5–6° C. or below) at the start of the reaction adds refrigeration costs to the operation. Previous attempts to synthesize propargyl bromide from phosphorus tribromide and propargyl alcohol in the absence of a base yielded large amounts of undesired side products; see L. Henry, *Chemische Berichte*, 1873, 6, 728.

It would be of considerable advantage if a way could be found of eliminating or at least significantly reducing formation of waxy solids in the process. It would be particularly advantageous if this could be done while avoiding the need for expensive refrigeration in the operation. An additional advantage would be the accomplishment of these things with a concomitant decrease in the formation of undesirable side products.

BRIEF SUMMARY OF THE INVENTION

This invention is deemed to enable achievement of the above advantages.

A feature of this invention is that propargyl bromide can be produced in good yield while minimizing the formation of undesired side products, such as 1,3-dibromopropene, 2,3-dibromopropene, and bromoallene. Surprisingly, this result can be achieved at higher addition temperatures than heretofore appreciated. And the process is economically advantageous, as a base such as pyridine or triethylamine is not required.

Provided by this invention is a process of producing propargyl bromide, which process comprises:

A) bringing together in a reaction zone under an inert atmosphere and in the absence of a base and in the presence of an inert diluent, a feed of phosphorus tribromide and a separate feed of propargyl alcohol thereby forming a reaction mixture;
B) while mechanically agitating the mixture being formed in A), maintaining the temperature of the mixture in the range of about 0° C. to about 25° C. to form a product mixture, and then
C) raising the temperature of the product mixture to a temperature in the range of about 40° C. to about 60° C. while stirring the product mixture for a ride period of at least about 2.5 hours.

Such process can be conducted as a batch process, as a semi-batch process, or as a continuous process.

Other embodiments and features of this invention will become still further apparent from the ensuing description and appended claims.

FURTHER DETAILED DESCRIPTION

When conducting a process in accordance with this invention there are basically two ways of bringing the reactants together in the reaction zone. One way is to feed the propargyl alcohol to the reaction zone and then feed the $PBr_3$ to the propargyl alcohol in the reaction zone. In such case, it matters not how or when the diluent is introduced into the reaction zone as long as at least sufficient diluent is present when the $PBr_3$ and propargyl alcohol are coming together in the reaction zone to serve as a heat sink for the heat of reaction evolved. Thus it is convenient to introduce all of the diluent before starting the feed of the $PBr_3$, or to introduce a substantial portion of the diluent before starting the feed of the $PBr_3$ and to introduce additional diluent along with the feed of $PBr_3$, either as a preformed solution of $PBr_3$ in the diluent, or as separate but concurrent feeds of $PBr_3$ and of diluent.

The second way of bringing the reactants together in the reaction zone is to feed propargyl alcohol and $PBr_3$ separately but concurrently into the reaction zone. Here again it matters not how or when the diluent is introduced into the reaction zone as long as at least sufficient diluent is present to serve as a heat sink for the heat of reaction evolved when the $PBr_3$ and propargyl alcohol are coming together in the reaction zone. For example, all of the diluent can be introduced into the reaction zone before starting the separate but concurrent feeds of the $PBr_3$ and of the propargyl alcohol. Alternatively, a substantial portion of the diluent can be introduced into the reaction zone before starting the concurrent feeds and additional diluent can accompany either or both such concurrent feeds. In other words, additional diluent maybe introduced as a preformed solution of $PBr_3$ in the diluent, as a preformed solution of propargyl alcohol in the diluent, and/or as a separate but concurrent feed with the concurrent feeds of $PBr_3$ and of propargyl alcohol.

In any event, the point at which the propargyl alcohol and the phosphorus tribromide come into contact with each other is part of the reaction zone. Preferably, the reactants are concurrently fed into a reaction zone composed of at least one reactor in which all of the components—whether fed individually or in any subcombination(s)—all come together for the first time and in which the process is initiated and carried out.

When the propargyl alcohol and the phosphorus tribromide come into contact with each other, the mechanical agitation can be accomplished by the use of, for example, jet mixers or static mixers. Optionally, high shear mechanical agitation and/or high speed jet dip legs may also be used.

The use of the term "concurrent" does not exclude the possibility of inconsequential interruptions taking place during the feeds. Nor does this term imply that the feeds must start at exactly the same moment in time. In the case of a co-feed process, the two feeds can be initiated with an interval of time between such initiation as long as the interval is sufficiently short as to cause no material adverse effect upon the overall process. Likewise in the case of a tri-feed or multi-feed operation, there maybe one or two different time intervals between or among the respective feeds, again provided that the time intervals are of sufficiently short duration to cause no material adverse effect upon the overall process.

The processes of this invention, whether performed in a batch mode, semi-batch (semi-continuous) mode, or continuous mode, are preferably conducted so that such things as the feeds, reaction, and maintenance of the desired temperature occur "continuously" during the reaction. However, it cannot be stressed strongly enough that one must not gain the impression that inconsequential interruption in one or more of such things cannot occur. Interruptions which do not materially affect the conduct of the process are not excluded from the scope of this invention. Whatever the terms used, the process should be conducted as one of ordinary skill in the art would carry out the processes after a thorough, unbiased reading of this entire disclosure and in keeping with the spirit of the invention gained from such a reading.

As is well known in the art, operation under an inert atmosphere requires the presence of an inert gas such as nitrogen, argon, or helium. This minimizes or excludes oxygen from the reaction zone. Nitrogen is a preferred inert gas in the practice of this invention. The inert gas can be introduced into the reaction zone by various means, such as sweeping the reaction zone with an inert gas prior to the introduction of the inert diluent, or passing the inert gas into the reaction zone during the process.

The inert diluent used is typically one or more (i) paraffinic hydrocarbons, (ii) cycloparaffinic hydrocarbons, or (iii) aromatic hydrocarbons or a mixture of any two or all three of (i), (ii) and (iii), but can be any inert liquid, i.e., a liquid which does not react with either the reactants or the products produced in the reaction in such a way as to prevent formation of propargyl bromide. Thus a diluent that solvates or complexes with a reactant or product of the reaction can be used provided that the formation of propargyl bromide is not prevented by its use; such a diluent is deemed to be inert within the meaning of this disclosure.

Because propargyl bromide is a high energy material that is sensitive to physical shock or impact, and that is also susceptible to rapid thermal decomposition upon exposure to high temperatures or fires, it is preferred to employ an inert solvent which forms an azeotrope with propargyl bromide, such as a paraffinic and/or cycloparaffinic hydrocarbon solvent that forms an azeotrope with propargyl bromide. By "azeotrope" is meant a mixture that under temperature and pressure conditions encountered at any normal stage of the life-cycle of propargyl bromide, the propargyl bromide and a stabilizing amount of the hydrocarbon when in the liquid or vapor state remain together at all times. Also when propargyl bromide is to be used as a fumigant, especially as a soil fumigant, it is desirable that the diluent used in the process be an environmentally-acceptable azeotropic inert liquid solvent that remains with and protects the propargyl bromide against hazardous shock-induced or thermally-induced decomposition whether the propargyl bromide is in the liquid state or in the vapor state.

By "environmentally-acceptable" is meant that the inert liquid satisfies or, if not yet evaluated, will satisfy the requirements for listing as an "inert" or "other ingredients" in categorized List 1, List 2, List 3, or List 4 of the Office of Pesticide Programs of the United States Environmental Protection Agency, such lists as updated Jun. 12, 2001. Such lists are incorporated herein by reference as if fully set forth herein, except that all substances on such lists which do not meet all criteria specified herein are excluded from such lists because they are incapable or unsuitable for use herein. The features of this paragraph are more fully described in commonly-owned copending application Ser. Nos. 10/118, 290, filed Apr. 8,2002, and 10/126,260, filed Apr. 18, 2002.

Various azeotropic solvents can be used in the practice of this invention. Non-limiting examples include n-heptane, mixed heptane isomers, cyclohexane, methylcyclohexane, 2-methylhexane, 2,4-dimethylpentane, n-octane, isooctane, 2-methylheptane, 2,2-dimethylhexane, isopropyl alcohol, and a mixture of cyclohexane and isopropyl alcohol. A preferred solvent mixture is composed of a mixture of $C_{7-9}$ hydrocarbons (e.g., Isopar E, ExxonMobil Chemical Corporation) in admixture with cyclohexane. A particularly preferred azeotropic solvent is a mixture composed primarily of $C_8$ isoparaffinic hydrocarbons such as Isopar C (ExxonMobil Chemical Corporation).

Mechanically agitating the reaction mixture being formed minimizes localized heat buildup in the reaction zone, ensures good mixing, and might minimize formation of undesired side products. Without wishing to be bound by theory, it is believed that good agitation may be important for achieving a decrease in undesired side products. At higher temperatures, the use of agitation to prevent heat buildup becomes increasingly important. On the laboratory scale, agitation rates are normally in the range of about 15 rpm to about 20 rpm.

During the bringing together of the phosphorus tribromide and the propargyl alcohol, the temperature of the reaction mixture being formed needs to be controlled, because of the exothermicity of the reaction of phosphorus tribromide and propargyl alcohol, and because of the thermal sensitivity of the propargyl bromide being formed. The temperature is maintained in the range of about 0° C. to about 25° C., and preferably in the range of from about 5° C. to about 20° C. Preferably, the temperature is continuously maintained in the desired range. While it is possible to perform the addition at temperatures above 25° C., it is not recommended for safety reasons and because the yield of propargyl bromide decreases. For a description of the sensitivities of propargyl bromide to shock and to thermal decomposition, see D. R. Forshey et al., *Fire Technology*, 1969 5 100–111.

A molar excess of phosphorus tribromide can increase the yield of propargyl bromide. Thus, preferably, a stoichiometric excess of phosphorus tribromide relative to propargyl alcohol is used. This can be accomplished using either of the two ways described above of bringing the propargyl alcohol and the phosphorus tribromide together. When propargyl alcohol is fed to the reaction zone before phosphorus tribromide, phosphorus tribromide is fed until the desired excess has been added to the reaction zone. When propargyl alcohol and phosphorus tribromide are fed separately but concurrently to the reaction zone, the phosphorus tribromide is fed in an amount that is a molar excess relative to the amount of propargyl alcohol being fed to form the reaction mixture. The amount of molar excess of phosphorus tribromide is preferably in the range of about 3% to about 15% relative to propargyl alcohol. More preferably, the phosphorus tribromide is in the range of about 5% to about 10% molar excess relative to propargyl alcohol.

Raising of the temperature of the product mixture and subjection of the product mixture to the ride period can occur in the reaction zone where the product mixture was formed, or in a different location (e.g., another reactor or vessel). For the ride period, ride times are typically at least about 2.5 hours on the laboratory scale. During the ride time, the temperature is usually in the range of about 40° C. to about 60° C. Preferably, the temperature during the ride period is in the range of about 40° C. to about 55° C. Primarily for safety reasons, it is highly preferred to keep the ride period temperature no higher than about 50° C.

The following Examples are presented to illustrate the practice of, and advantages made possible by, this invention. These Examples are not intended to limit, and should not be construed as limiting, the scope of this invention to the particular operations or conditions described therein.

EXAMPLES

All Examples were performed under an atmosphere of nitrogen, with nitrogen bubbling. A summary of the results of all of the Examples is presented in Table 1.

Example 1

Isopar C (343 g) was charged to a reactor. Propargyl alcohol (175 g, 3.1 mol) and phosphorus tribromide (295.7 g, 1.09 mol) were fed separately but concurrently to the reactor at feed rates of about 2.5 mL/minute, while maintaining the temperature of the reaction mixture in the reactor at 6° C. Addition lasted for about 43 minutes, during which time this reaction mixture was stirred at a rate of 17 rpm. The reaction mixture was warmed to 50° C. and allowed to ride, with stirring, for 3 hours at 50° C. The mixture was then washed twice with water (10.7 g and 10 g), and the solution was allowed to stand to form aqueous and organic layers; the layers were separated. The organic layer was analyzed by NMR. The yield of propargyl bromide was 64.37%. The solution also contained 10.26% 2,3-dibromopropene, 2.54% 1,3-dibromopropene, but no bromoallene.

Example 2

Another run using the procedure of Example 1 was performed, except that the temperature of the reaction mixture in the reactor was maintained at 20° C. during the feeding of the propargyl alcohol and the phosphorus tribromide. The yield of propargyl bromide was 62.1%. The solution also contained 10.14% 2,3-dibromopropene, 3.6% 1,3-dibromopropene, and 1.22% bromoallene.

Example 3

Three runs using the procedure of Example 1 were performed, except that the amount of phosphorus tribromide was 304.2 g (1.12 mol), the feed rates of the propargyl alcohol and phosphorus tribromide were about 2.2 mL/minute (resulting in an addition time of about 55 minutes), stirring rate was 18 rpm, the ride time at 50° C. was varied, and the water wash was 135 g (plus 50 g Isopar C). Results for the three runs are summarized in Table 1.

Example 4

Toluene (50.0 g) and propargyl alcohol (20.0 g, 0.357 mol) were charged to a round-bottom flask. Phosphorus tribromide (11.9 mL, 33.9 g, 0.125 mol) was fed to the flask while maintaining the temperature of the contents of the flask at 3° C. During the initial part of the addition, the temperature rose to 15° C. before returning to 3° C. Addition lasted for about 15 minutes, during which this reaction mixture was stirred. The reaction mixture was warmed to 50° C. and allowed to ride, with stirring, for 3 hours at 50° C. The mixture was then washed with water (29.61 g), and stirred for 10 minutes at a rate of 250 rpm. The mixture was then allowed to stand to form aqueous and organic layers; the layers were separated. The organic layer was analyzed by $^1$H NMR. The yield of propargyl bromide was 78.81%. The solution also contained 14.78% 2,3-dibromopropene, 3.17% 1,3-dibromopropene, and 1.38% bromoallene.

TABLE 1

| Ex. | Run | Addition temp. | Propargyl bromide yield | Bromoallene | 2,3-dibromopropene | 1,3-dibromopropene | Molar excess PBr$_3$ | Ride time at 50° C. |
| --- | --- | --- | --- | --- | --- | --- | --- | --- |
| 1 | — | 6° C. | 64.37% | 0 | 10.26% | 2.54% | 5% | 3 hr. |
| 2 | — | 20° C. | 62.1% | 1.22% | 10.14% | 3.6% | 8% | 3 hr. |
| 3 | a | 6° C. | 66.27% | 2.24% | 10.33% | 2.88% | 8% | 3 hr. |
| 3 | b | 6° C. | 67.52% | 2.31% | 10.39% | 2.94% | 8% | 5 hr. |
| 3 | c | 6° C. | 66.54% | 2.31% | 10.84% | 2.91% | 8% | 16 hr. |
| 4 | — | 0° C. | 78.81% | 1.38% | 14.78% | 3.17% | 5% | 3 hr. |

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions specified in this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as maybe expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing propargyl bromide, which process comprises:

A) bringing together in a reaction zone under an inert atmosphere and in the absence of a base and in the presence of an inert diluent, a feed of phosphorus tribromide and a separate feed of propargyl alcohol thereby forming a reaction mixture;

B) while mechanically agitating the mixture being formed in A), maintaining the temperature of the mixture in the range of about 0° C. to about 25° C. to form a product mixture, and then C) raising the temperature of the product mixture to a temperature in the range of about 40° C. to about 60° C. while stirring the product mixture for a ride period of at least about 2.5 hours.

2. A process according to claim 1 wherein said feed of phosphorus tribromide and said separate feed of propargyl alcohol are fed concurrently to said reaction zone.

3. A process according to claim 1 wherein said separate feed of propargyl alcohol is fed to the reaction zone and then said feed of phosphorus tribromide is fed to the reaction zone.

4. A process according to claim 1 wherein said inert diluent is a paraffinic and/or cycloparaffinic hydrocarbon solvent that forms an azeotrope with propargyl bromide.

5. A process according to claim 4 wherein said paraffinic and/or cycloparaffinic hydrocarbon solvent is a mixture of $C_{7-9}$ hydrocarbons.

6. A process according to claim 4 wherein said paraffinic and/or cycloparaffinic hydrocarbon solvent is a mixture composed primarily of $C_8$ isoparaffinic hydrocarbons.

7. A process according to claim 1 wherein mechanically agitating the mixture in B) is accomplished by use of a jet mixer or a static mixer.

8. A process according to claim 1 wherein the temperature in B) is in the range of about 5° C. to about 20° C.

9. A process according to claim 1 wherein the temperature in C) is in the range of about 40° C. to about 55° C.

10. A process according to claim 1 wherein said inert atmosphere is comprised of nitrogen.

11. A process according to claim 1 wherein a molar excess of phosphorus tribromide relative to propargyl alcohol is used.

12. A process according to claim 11 wherein said molar excess is in the range of about 3% to about 15%.

13. A process according to claim 11 wherein said molar excess is in the range of about 5% to about 10%.

14. A process according to claim 1 wherein said inert diluent is a paraffinic and/or cycloparaffinic hydrocarbon solvent that forms an azeotrope with propargyl bromide, and is a mixture of $C_{7-9}$ hydrocarbons; wherein the temperature in B) is in the range of about 5° C. to about 20° C.; and wherein a molar excess of phosphorus tribromide relative to propargyl alcohol is used, and said molar excess is in the range of about 5% to about 10%.

15. A process according to claim 14 wherein said process is conducted as a continuous process.

16. A process according to claim 1 wherein said inert diluent is a paraffinic and/or cycloparaffinic hydrocarbon solvent that forms an azeotrope with propargyl bromide, and is a mixture composed primarily of $C_8$ isoparaffinic hydrocarbons; wherein the temperature in B) is in the range of about 5° C. to about 20° C.; and wherein a molar excess of phosphorus tribromide relative to propargyl alcohol is used, and said molar excess is in the range of about 5% to about 10%.

17. A process according to claim 16 wherein said process is conducted as a continuous process.

18. A process according to claim 1 wherein said process is conducted as a batch process.

19. A process according to claim 1 wherein said process is conducted as a continuous process.

20. A process according to claim 1 wherein said process is conducted as a semi-batch process.

* * * * *